US010470982B2

(12) United States Patent
Shimosoyama et al.

(10) Patent No.: US 10,470,982 B2
(45) Date of Patent: Nov. 12, 2019

(54) CURABLE SILICONE COMPOSITION HAVING OPTICAL TRANSPARENCY AND METHOD OF FABRICATING MOLDED MATERIAL OF PHOTOCURABLE RESIN USING THE SAME

(71) Applicant: SHOFU INC., Kyoto-shi, Kyoto (JP)

(72) Inventors: Shun Shimosoyama, Kyoto (JP); Toshio Kitamura, Kyoto (JP)

(73) Assignee: SHOFU INC., Kyoto (JP)

( * ) Notice: Subject to any disclaimer, the term of this patent is extended or adjusted under 35 U.S.C. 154(b) by 737 days.

(21) Appl. No.: 14/497,835

(22) Filed: Sep. 26, 2014

(65) Prior Publication Data

US 2015/0108694 A1 Apr. 23, 2015

(30) Foreign Application Priority Data

Oct. 18, 2013 (JP) ................................. 2013-217288

(51) Int. Cl.
| | |
|---|---|
| *A61K 6/093* | (2006.01) |
| *C08L 83/04* | (2006.01) |
| *C08K 3/36* | (2006.01) |
| *C08K 5/56* | (2006.01) |
| *C08L 83/00* | (2006.01) |
| *A61K 6/00* | (2006.01) |

(52) U.S. Cl.
CPC ................ *A61K 6/093* (2013.01); *C08K 3/36* (2013.01); *C08K 5/56* (2013.01); *C08L 83/00* (2013.01); *C08L 83/04* (2013.01); *A61K 6/0002* (2013.01); *A61K 6/0005* (2013.01); *A61K 6/0088* (2013.01); *C08L 2312/06* (2013.01)

(58) Field of Classification Search
None
See application file for complete search history.

(56) References Cited

U.S. PATENT DOCUMENTS

| | | | | |
|---|---|---|---|---|
| 5,066,714 A | * | 11/1991 | Inoue ....................... | A61K 6/10 524/267 |
| 5,403,885 A | * | 4/1995 | Voigt ....................... | A61K 6/10 264/18 |
| 2011/0140289 A1 | * | 6/2011 | Shiobara ................. | C08K 3/34 257/789 |
| 2012/0225402 A1 | * | 9/2012 | Crivello ............... | A61C 19/066 433/37 |
| 2013/0026682 A1 | | 1/2013 | Rist et al. | |
| 2013/0210958 A1 | | 8/2013 | Shimosoyama et al. | |
| 2014/0088232 A1 | * | 3/2014 | Mochizuki .............. | H01L 33/56 524/261 |

FOREIGN PATENT DOCUMENTS

| | | |
|---|---|---|
| CN | 102153863 | 8/2011 |
| CN | 103239363 | 8/2013 |
| JP | 5-194860 | 8/1993 |
| JP | H05-194860 A | 8/1993 |
| JP | 09-002916 | 1/1997 |
| JP | 2013-519547 A | 5/2013 |
| JP | 2013-177387 A | 9/2013 |
| WO | WO 2013/076450 * | 5/2013 |

OTHER PUBLICATIONS

"Dynamic Mechanical Analysis: A" Dynamic Mechanical Analysis: A Practical Introduction Second Addition, authored by Menard and published by the CRC Press (2008).*
Viscopedia internet site (no date) http://www.viscopedia.com/basics/types-of-viscosity/.*
European Search Report dated Mar. 3, 2015, 7 pages.
Office Action dated Apr. 28, 2018 in Chinese Application No. 201410083640.3, with English translation.

* cited by examiner

*Primary Examiner* — Marc S Zimmer
(74) *Attorney, Agent, or Firm* — Wenderoth, Lind & Ponack, L.L.P.

(57) ABSTRACT

Provided herein is a curable silicone composition that has high optical transparency after being cured and that is in a putty form to be hand-mixable. A curable silicone composition contains: a specific organopolysiloxane as a component (1); a specific organohydrogenpolysiloxane as a component (2); a filler as a component (3); and a catalyst as a component (4). The difference between the refractive index of one of the components (1) to (3) that has the highest refractive index and the refractive index of one of the components (1) to (3) that has the lowest refractive index is 0.1000 or less. The complex viscosity of any of constituent compositions of the curable silicon composition before the curable silicone composition is cured is 10 Pa·s to 100000 Pa·s, as measured under predetermined measurement condition.

14 Claims, No Drawings

CURABLE SILICONE COMPOSITION HAVING OPTICAL TRANSPARENCY AND METHOD OF FABRICATING MOLDED MATERIAL OF PHOTOCURABLE RESIN USING THE SAME

TECHNICAL FIELD

The present invention relates to a curable silicone composition having optical transparency and a method of fabricating a molded material of a photocurable resin using the curable silicone composition, and more particularly to a hand-mixable curable silicone composition having optical transparency and a method of fabricating a molded material of a photocurable resin using the hand-mixable curable silicone composition.

BACKGROUND ART

When a tooth substance in an oral cavity is partially removed because of caries or the like, a treatment in which an original tooth crown morphology is restored using a variety of materials is commonly performed to recover the lost tooth substance aesthetically, functionally, and morphologically. Methods to restore a tooth crown morphology are roughly divided into two types according to the operator. A first type of the methods is performed by a dentist at a dental clinic. The dentist removes a portion of the tooth substance with a disease, and thereafter repairs a tooth crown morphology using a photocurable resin. Another type of the methods is performed by a dental technician at a dental laboratory. In this method, a portion of the tooth substance with a disease is removed at a dental clinic, and thereafter an impression of the portion is taken in the oral cavity to obtain a concave mold. Information on the obtained concave mold is sent to the dental laboratory, and the dental technician fabricates a dental prosthetic restoration based on the information. The treatment method is selected as appropriate by the dentist. In general, if the amount of the removed tooth substance is large and the morphology to be restored is complicated, such as a case where the tooth substance is removed from the entire tooth crown portion or a large number of teeth, the treatment in which a prosthetic restoration fabricated by the dental technician is used is selected.

Various materials are used for the dental prosthetic restoration fabricated by the dental technician. Examples of the material include inorganic materials such as zirconia and porcelain, metal, and photocurable resins. The material is selected according to the medical policy or an aesthetic request from the patient. Prosthetic restorations fabricated using inorganic materials such as zirconia and porcelain are highly aesthetic and functional compared to prosthetic restorations fabricated using metal or photocurable resins. For prosthetic restorations fabricated using metal or photocurable resins, in general, metal is used for portions for which the patient does not make a strict aesthetic request such as posterior teeth, and photocurable resins in a tooth crown color are used for portions for which the patient makes a strict aesthetic request such as anterior teeth.

To fabricate a prosthetic restoration using a photocurable resin, the dental technician builds up the photocurable resin on a metal frame serving as a base using a dedicated instrument. A tooth crown morphology and an occlusal morphology similar to those of the natural teeth are significantly complicated, and thus require much expertise and high technical capabilities to be fabricated by the build-up method, and take a long time to be fabricated.

Therefore, there is also used a method in which a dentist or a dental technician makes a concave mold inside or outside an oral cavity using a silicone impression material for bite registration or for indirect bonding and thereafter a tooth crown morphology or an occlusal morphology is restored using a photocurable resin. Examples of the silicone impression material for bite registration or for indirect bonding according to the related art include the following.

JP05-194860A discloses a composition for bite registration containing a highly dispersible filler subjected to a hydrophobizing treatment, short-chain organopolysiloxane having two or more vinyl groups in a molecule, a short-chain QM resin having some vinyl groups, organopolysiloxane having two or more vinyl groups in a molecule, organohydrogenpolysiloxane serving as a cross-linking agent, a catalyst, and a dye. The composition expresses high optical transparency, tearing strength, and rubber hardness after being cured.

JP09-002916A discloses a composition containing: polyorganosiloxane containing 5 to 60% by weight of substantially straight-chain polydiorganosiloxane with an average degree of polymerization of 3000 to 20000, 10 to 40% by weight of branched polyorganosiloxane or cyclic polyorganosiloxane including a branch, and the remaining percentage of straight-chain polydiorganosiloxane with an average degree of polymerization of 5 to 1000, the polyorganosiloxane having two or more vinyl groups bonded to a silicon atom in a molecule; polyorganosiloxane having three or more hydrogen atoms bonded to a silicon atom in a molecule; and a platinum-based compound. The composition provides good mixability and extrudability with its paste hardly dripping before being cured, and keeps high optical transparency after being cured.

SUMMARY OF INVENTION

Technical Problem

The optically transparent silicone composition according to the related art described in JP05-194860A is intended to bite registration. Meanwhile, the optically transparent silicone composition according to the related art described in JP09-002916A is intended to place an orthodontic bracket. The optically transparent silicone compositions according to JP05-194860A and JP09-002916A are greatly different from the present invention in the intended usage. Although the optically transparent silicone compositions are optically transparent, the compositions are hardly hand-mixable because the compositions are low in viscosity before being cured, and are not provided in a putty form. Therefore, in order to mix the optically transparent silicone compositions, it is essential to fill the compositions into a dedicated package and use a mixing instrument. The silicone compositions according to the related art which are filled into a dedicated package to be mixed using a dedicated instrument are significantly costly compared to silicone compositions in a putty form, and disadvantageously too expensive to be routinely used at a dental laboratory.

It is an object of the present invention to provide a curable silicone composition that has high optical transparency after being cured and that is in a putty form to be hand-mixable.

Solution to Problem

In order to address the foregoing issues, the inventors made an earnest study to find that a hand-mixable curable silicone composition in a putty form having high optical transparency can be obtained. The mixable curable silicone composition is comprised of two or more types of constituent compositions containing: organopolysiloxane having at least two unsaturated groups in a molecule as a component (1); organohydrogenpolysiloxane having at least two SiH groups in a molecule as a component (2); a filler as a component (3); and a catalyst as a component (4).

The difference between the refractive index of one of the components (1) to (3) that has the highest refractive index and the refractive index of one of the components (1) to (3) that has the lowest refractive index is 0.1000 or less. The complex viscosity of any of the constituent compositions of the curable silicon composition before the curable silicone composition is cured is 10 Pa·s to 100000 Pa·s, as measured at a stage temperature of 23° C., a strain amount of 1%, and a frequency of 0.1 Hz to 100 Hz, by frequency dispersion measurement at an angular frequency of 25 rad/s. In addition, the inventors found that a molded material of a photocurable resin to which the form of an object has been duplicated was easily made by: preparing such a curable silicone composition by hand mixing, making a concave mold by pressing the prepared curable silicone composition onto the object and curing the curable silicone composition; and filling the concave mold with a photocurable resin and illuminating the photocurable resin with light via the cured silicone composition. The present invention has been made based on the above findings.

DESCRIPTION OF EMBODIMENTS

The present invention improves a mixable curable silicone composition comprised of two or more types of constituent compositions containing: organopolysiloxane having at least two unsaturated groups in a molecule as a component (1); organohydrogenpolysiloxane having at least two SiH groups in a molecule as a component (2); a filler as a component (3); and a catalyst as a component (4). In the present invention, the difference between the refractive index of one of the components (1) to (3) that has the highest refractive index and the refractive index of one of the components (1) to (3) that has the lowest refractive index is 0.1000 or less. In the present invention, further, the complex viscosity of any of the constituent compositions of the curable silicon composition before the curable silicone composition is cured is 10 Pa·s to 100000 Pa·s. The complex viscosity is measured at a stage temperature of 23° C., a strain amount of 1%, and a frequency of 0.1 Hz to 100 Hz, by frequency dispersion measurement at an angular frequency of 25 rad/s.

The component (1) is organopolysiloxane having at least two unsaturated groups in a molecule, and more particularly organopolysiloxane in which the unsaturated groups are organic groups having an ethylenically unsaturated double bond.

The organopolysiloxane is represented by the formula [1]:

<Formula 1>

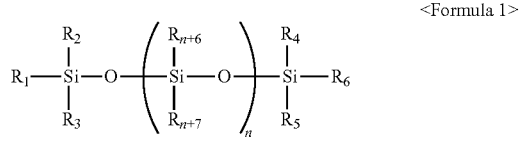

In the formula, $R_1$ to $R_{n+7}$ are straight-chain, branched, or cyclic unsubstituted or substituted organic groups that are the same as or different from each other, and it is essential that at least two of $R_1$ to $R_{n+7}$ must be unsaturated groups. In addition, n is an integer of 1 or more. $R_{n+6}$ and $R_{n+7}$ may be the same as or different from each other for every repeating unit, and are not specifically limited.

Specific examples of the organic groups other than the unsaturated groups include, but are not limited to, a methyl group, an ethyl group, a phenyl group, a benzyl group, a tolyl group, a xylyl group, a biphenyl group, an ether group, an epoxy group, and an alicyclic epoxy group. Such groups may be partially substituted by other groups. Among the organic groups, a methyl group and a phenyl group are particularly preferable, and choice of such organic groups enhances the optical transparency of the composition after being cured.

The type of the at least two unsaturated groups provided in a molecule is not specifically limited. However, organic groups having an ethylenically unsaturated double bond are preferable, and so-called vinyl groups having an ethylenically unsaturated double bond directly bonded to a silicon atom are particularly preferable. The unsaturated groups may be located in any monomer unit of the organopolysiloxane. However, the unsaturated groups are preferably located at or near the terminal end of the main chain of the organopolysiloxane. Further, it is particularly preferable that the organic groups having an ethylenically unsaturated double bond should be located at the α and ω positions, that is, at the two terminal ends of the main chain, one organic group at each terminal end. Use of such organopolysiloxane facilitates formation of a three-dimensional network structure and expresses high rubber hardness.

The molecular structure of the organopolysiloxane is not specifically limited, and may be any of straight-chain, cyclic, branched, and three-dimensional network structures.

Specific examples of component (1) include divinylpolydimethylsiloxane, phenyl-modified divinylpolysiloxane, benzyl-modified divinylpolysiloxane, tolyl-modified divinylpolysiloxane, xylyl-modified divinylpolysiloxane, biphenyl-modified divinylpolysiloxane, ether-modified divinylpolysiloxane, epoxy-modified divinylpolysiloxane, alicyclicepoxy-modified divinylpolysiloxane, and mixtures of two or more of them or the like. Among these, phenyl-modified divinylpolysiloxane is especially preferable.

The refractive index of the component (1) is preferably 1.400 to 1.500, more preferably 1.450 to 1.480, further more preferably 1.460 to 1.470. If the refractive index of the component (1) is outside the above range, there may be a significant difference between the refractive index of the component (1) and the refractive indexes of other components contained in the curable silicone composition according to the present invention, and high optical transparency may not be obtained.

The quantity of the component (1) is preferably 1 wt % to 80 wt %, more preferably 5 wt % to 80 wt %, particularly preferably 5 wt % to 30 wt %, in the total curable silicone composition. If the quantity of the component (1) is less than 1 wt %, a hydrosilylation reaction may not sufficiently proceeds, which may degrade curability. If the quantity of the component (I) is more than 80 wt %, meanwhile, the quantity of the component (3) as a filler is relatively decreased, which makes it difficult to obtain the resulting composition in a putty form to be hand-mixable.

Use of such a component (1) makes it possible to obtain a curable silicone composition that has good optical transparency, that is easily hand-mixable, that has a non-sticky paste surface, and that has appropriate properties such as hardness after being cured.

The component (2) is organohydrogenpolysiloxane having at least two SiH groups in a molecule, and is subjected to a hydrosilylation addition reaction with the component (1) to act as a cross-linking agent capable of curing the curable silicone composition.

The organohydrogenpolysiloxane is represented by the formula [2]:

<Formula 2>

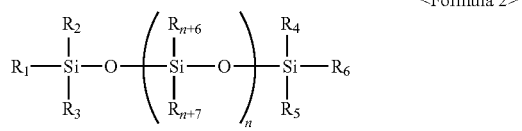

In the formula, $R_1$ to $R_{n+7}$ are straight-chain, branched, or cyclic unsubstituted or substituted organic groups that are the same as or different from each other, and it is essential that at least two of $R_1$ to $R_{n+7}$ must be hydrogen atoms. In addition, n is an integer of 1 or more. $R_{n+6}$ and $R_{n+7}$ may be the same as or different from each other for every repeating unit, and are not specifically limited.

Specific examples of the organic groups include, but are not limited to, a methyl group, an ethyl group, a phenyl group, a benzyl group, a tolyl group, a xylyl group, a biphenyl group, an ether group, an epoxy group, and an alicyclic epoxy group. Such groups may be partially substituted by other groups. Among the organic groups, a methyl group and a phenyl group are particularly preferable, and choice of such organic groups enhances the optical transparency of the composition after being cured.

In addition, the at least two hydrogen atoms directly bonded to a silicon atom provided in a molecule may be located in any monomer unit of the organohydrogenpolysiloxane. Use of such organohydrogenpolysiloxane facilitates formation of a three-dimensional network structure and expresses high rubber hardness.

The content of the SiH groups in the component (2) is preferably in the range of 1 mol to 6 mol with respect to 1 mol of the unsaturated groups in the component (1). If the content of the SiH groups in the component (2) is less than the lower limit of the above range, the obtained curable silicone composition may not be sufficiently cured. If the content of the SiH groups in the component (2) is more than the upper limit of the above range, on the other hand, the obtained curable silicone composition may be so hard and a large number of cracks may be formed in the surface.

The molecular structure of the organohydrogenpolysiloxane is not specifically limited, and may be any of straight-chain, cyclic, branched, and three-dimensional network structures.

Specific examples of component (2) include dimethylhydrogenpolysiloxane, phenyl-modified organohydrogenpolysiloxane, benzyl-modified organohydrogenpolysiloxane, tolyl-modified organohydrogenpolysiloxane, xylyl-modified organohydrogenpolysiloxane, biphenyl-modified organohydrogenpolysiloxane, ether-modified organohydrogenpolysiloxane, epoxy-modified organohydrogenpolysiloxane, alicyclicepoxy-modified organohydrogenpolysiloxane and mixtures of two or more of them or the like. Among these, phenyl-modified organohydrogenpolysiloxane is especially preferable.

The refractive index of the component (2) is preferably 1.400 to 1.500, more preferably 1.450 to 1.480, further more preferably 1.460 to 1.470. If the refractive index of the component (2) is outside the above range, there may be a significant difference between the refractive index of the component (2) and the refractive indexes of other components contained in the curable silicone composition according to the present invention, and high optical transparency may not be obtained.

The quantity of the component (2) is preferably in the range of 0.01 wt % to 30 wt % in the total curable silicone composition. If the quantity of the component is less than 0.01 wt %, a hydrosilylation reaction may not sufficiently progress, which may degrade curability. If the quantity of the component is more than wt %, meanwhile, a hydrosilylation reaction may rapidly proceed, which may significantly shorten the time for which the resulting curable silicone composition has flowability enough to be workable. Moreover, the obtained curable silicone composition may be so hard and a large number of cracks may be formed in the surface.

Use of such a component (2) makes it possible to obtain a curable silicone composition that has good optical transparency, that is easily hand-mixable, that has a non-sticky paste surface, and that has appropriate properties such as hardness after being cured.

The component (3) is a filler, and keeps the curable silicone composition before being cured in a putty form to be hand-mixable, and improves the ease of handling of the curable silicone composition and the physical properties of the curable silicone composition after being cured.

The shape of the component (3) as a filler is not specifically limited, but is preferably spherical rather than indefinite. If the component (3) has an indefinite shape, not only the mixability and the flowability of a mixture may be reduced, but also the optical transparency may be adversely affected. Use of spherical particles makes it possible to obtain a curable silicone composition that provides a mixture with light mixability and improved flowability and that is easily workable. The terms "spherical shape" and "indefinite shape" as used herein refer to the shape of particles observed in a photograph captured using a scanning or transmission electron microscope. Particles having a round shape and a uniformity ratio, which is obtained by dividing the minimum diameter by the maximum diameter, of 0.6 or more are determined to have a spherical shape, and other particles are determined to have an indefinite shape.

Specific examples of component (3) include aluminum, aluminite, potassium bicarbonate, potassium chloride, potassium cyanide, sodium cyanide, barium fluoride, calcium fluoride, strontium fluoride, anhydrous silica, mordenite, clinoptilolite, zeolite, diatomaseous earth, fired diatomaseous earth, activated clay, quartz, fused quartz, synthetic silica, aluminosilicate glass, borosilicate glass, soda lime silicate glass, titania silica glass, crystal, soda ashes, opal, polyvinylidene fluoride, methyl methacrylate resin, polymethylmethacrylate, vinyl acetate resin, poly-trifluorochloroethylene, stearic acid, white carbon, silicone rubber powder, silicone resin powder, fumed silica and mixtures of two or more of them or the like. It is especially preferable to select from amorphous silica such as fused quartz, synthetic silica, aluminosilicate glass, borosilicate glass, soda-lime silicate glass, titania-silica glass or the like and mixtures of two or more of them.

Use of such a component (3) as a filler provides a refractive index that is close to the refractive indexes of other components to provide high optical transparency. The component (3) as a filler may be subjected to a surface treatment.

The particle size of the component (3) as a filler is not specifically limited, but the 50% particle size is preferably 0.1 µm or more, more preferably 0.1 µm to 100 µm, further more preferably 0.1 µm to 80 µm. The term "50% particle size" as used in the context of the present invention is also referred to as a "volume-based median size", and calculated based on particle size distribution measured by a laser-diffraction particle size distribution measuring device or the like. If the 50% particle size of the component is less than 0.1 µm, the paste surface may be sticky and the paste viscosity may be increased, which may reduce ease of handling.

The refractive index of the component (3) is preferably 1.400 to 1.500, more preferably 1.450 to 1.480, further more preferably 1.460 to 1.470. If the refractive index of the component (3) is outside the above range, there may be a significant difference between the refractive index of the component (3) and the refractive indexes of other components contained in the curable silicone composition according to the present invention, and high optical transparency may not be obtained.

The quantity of the component (3) is preferably 10 wt % to 95 wt %, more preferably 15 wt % to 90 wt %, furthermore preferably 50 wt % to 90 wt %, in the total curable silicone composition. If the quantity of the component is less than 10 wt %, the other liquid components contained in the curable silicone composition according to the present invention are relatively increased, which makes it difficult to obtain the resulting composition in a putty form to be hand-mixable. If the quantity of the component is more than 95 wt %, meanwhile, the obtained curable silicone composition may be so hard as to adversely affect mixability and flowability. Moreover, the quantities of the components (1) and (2) involved in a curing reaction are relatively decreased, and a hydrosilylation reaction may not sufficiently proceed, which may degrade curability.

Use of such a component (3) makes it possible to obtain a curable silicone composition that has good optical transparency, that is easily hand-mixable, that has a non-sticky paste surface, and that has appropriate properties such as hardness after being cured.

The curable silicone composition according to the present invention may contain fumed silica or the like as a reinforcing filler or a thickener, for example, and such a component may be subjected to a surface treatment. In addition, the reinforcing filler and the thickener are preferably subjected to conditions that are equivalent to those for the component (3) as a filler. The quantity of the reinforcing filler and the thickener is preferably 0.1 wt % to 50 wt % in the total curable silicone composition.

The component (4) is a catalyst, and is a hydrosilylation catalyst that promotes a hydrosilylation addition reaction between the unsaturated groups contained in the component (1) and the SiH groups contained in the component (2). Specific examples of the catalyst include platinum catalysts such as platinum black, platinum (II) chloride, a chloroplatinic acid, a reactant between a chloroplatinic acid and a monohydric alcohol, a complex between a chloroplatinic acid and olefines, and platinum bis(acetoacetate), platinum-group metal catalysts such as palladium-based catalysts and rhodium-based catalysts, and mixtures of two or more kinds thereof. Complexes of platinum and siloxane are particularly suitably used.

The refractive index of the component (4) is preferably 1.400 to 1.500, more preferably 1.450 to 1.480, further more preferably 1.460 to 1.470. If the refractive index of the component (4) is in the above range, no significant difference is caused between the refractive index of the component (4) and the refractive indexes of other components contained in the curable silicone composition according to the present invention, which makes it possible to obtain high optical transparency.

The quantity of the component (4) is preferably 0.005 wt % to 0.5 wt % in the total curable silicone composition. If the quantity of the component is less than 0.005 wt %, a hydrosilylation reaction may not sufficiently proceed, which may degrade curability. If the quantity of the component is more than 0.5 wt %, meanwhile, a hydrosilylation reaction may rapidly proceed, which may significantly shorten the time for which the resulting curable silicone composition has flowability enough to be workable.

Further, additional components such as a pigment, a reaction regulator, a defoaming agent, and a surfactant may be concurrently used to the extent that the effect of the present invention is not hindered.

The present invention provides a mixable curable silicone composition comprised of two or more types of constituent compositions. The number of types of constituent compositions to be mixed is not specifically limited, but is preferably two from the viewpoint of ease of handling of mixing work or the like. In particular, the curable silicone composition is preferably comprised of a constituent composition (base material) containing the component (1), the component (2), and the component (3) and a constituent composition (catalyst material) containing the component (1), the component (3), and the component (4). The mixing ratio between the constituent compositions is not specifically limited, and may be freely selected. In order to enable hand mixing, however, it is essential that the complex viscosity of at least one of the constituent compositions of the curable silicon composition before the curable silicone composition is cured is 10 Pa·s to 100000 Pa·s, as measured at a stage temperature of 23° C., a strain amount of 1%, and a frequency of 0.1 Hz to 100 Hz, by frequency dispersion measurement at an angular frequency of 25 rad/s. Among others, the complex viscosity of the at least one of the constituent compositions is preferably 50 Pa·s to 50000 Pa·s, further more preferably 1000 Pas to 50000 Pa·s. That is, if the complex viscosity of one of the constituent compositions before the curable silicone composition is cured is in the range of 10 Pa·s 100000 Pa·s, the characteristics of the curable silicone composition according to the present invention can be expressed even if the complex viscosity of the other constituent composition or the other constituent compositions before the curable silicone composition is cured is outside the above range.

More preferably, the complex viscosity of all of the constituent compositions before the curable silicone composition is cured is in the above range. If such a range is met, the resulting curable silicone composition is in a putty form with good mixability.

In a preferable aspect, not only the complex viscosity of the constituent compositions before the curable silicone composition is cured but also the complex viscosity of the final composition after the constituent compositions are mixed before the curable silicone composition is cured is in the above range.

In the curable silicone composition according to the present invention, the range of the content of each component, which contributes to expressing the above characteristics, is determined as follows. In the total curable silicone composition,
the component (1) accounts for 1 to 80 wt %;
the component (2) accounts for 0.01 to 30 wt %;
the component (3) accounts for 10 to 95 wt %; and
the component (4) accounts for 0.005 to 0.5 wt %.

By making the curable silicone composition of the components in amounts in such ranges, it is possible to provide a curable silicone composition that has good optical transparency and that is in a putty form to be easily hand-mixable.

The curable silicone composition according to the present invention is not limited to the above numerical ranges, and the curable silicone composition according to the present invention has high optical transparency and is in a putty form to be hand-mixable even if the above ranges are not met.

More preferably, in the total curable silicone composition,
the component (1) accounts for 5 to 80 wt %;
the component (2) accounts for 0.01 to 30 wt %;
the component (3) accounts for 15 to 90 wt %; and
the component (4) accounts for 0.005 to 0.5 wt %.

In addition to the effect described above, the curable silicone composition that meets such ranges achieves further higher optical transparency.

In addition, the curable silicone composition further facilitates fabrication of a dental prosthetic restoration from a photocurable resin using the curable silicone composition according to the present invention, and also shortens the time to be spent to fabricate it.

Furthermore preferably, in the total curable silicone composition,
the component (1) accounts for 5 to 30 wt %;
the component (2) accounts for 0.01 to 30 wt %;
the component (3) accounts for 50 to 90 wt %; and
the component (4) accounts for 0.005 to 0.5 wt %.

In addition to the effect described above, the curable silicone composition that meets such ranges not only achieves still higher optical transparency, but also suppresses stickiness of the paste before the curable silicone composition is cured, is lightly mixable, provides moderate flowability to the mixture, and optimizes properties such as hardness after the curable silicone composition is cured. Moreover, the curable silicone composition makes it possible not only to further facilitate fabrication of a dental prosthetic restoration by the method according to the present invention, and to further shorten the time to be spent to fabricate it, but also to observe air bubbles at the interface between the curable silicone composition and the photocurable resin when they are pressed onto each other, and to facilitate appropriate pressing that does not deform the curable silicone composition after being cured.

The curable silicone composition according to the present invention can be utilized as a concave mold for fabrication of a dental prosthetic restoration made from a photocurable resin, for example. In this case, if the optical transmittance of the silicone composition after being cured is too low, an amount of light enough to start a polymerization reaction of the photocurable resin may not transmit the silicone composition after being cured, and the polymerization reaction of the photocurable resin may not sufficiently proceed. In addition, the presence or absence of air bubbles and the flow of the photocurable resin may not be observed when the photocurable resin is poured into the concave mold of the curable silicone composition, and it may not be visually observed whether the fabricated dental prosthetic restoration appropriately restores a desired morphology.

Therefore, the curable silicone composition preferably has an optical transmittance of 50% or more at a wavelength of 470 nm after being cured. The curable silicone composition having such an optical transmittance can transmit an amount of light enough to reliably polymerize a photocurable resin injected into a concave mold obtained by curing the silicone composition. In addition, the presence or absence of air bubbles and the flow of the photocurable resin during pressing may be observed after the photocurable resin is injected into the concave mold, which advantageously makes it possible to visually observe whether the molded photocurable resin appropriately restores a desired morphology.

In order for the curable silicone composition according to the present invention to express the optical transparency described above, it is importance to control the refractive indexes of the components (1) to (4) contained in the curable silicone composition.

Preferably, the components (1) and (3) each have a refractive index of 1.450 to 1.480. If the components (1) and (3) each have a refractive index of 1.450 to 1.480, the components have similar refractive indexes to provide higher optical transparency.

More preferably, the components (1) to (3) each have a refractive index of 1.450 to 1.480. If the components (1) to (3) each have a refractive index of 1.450 to 1.480, the components (1) to (3) have similar refractive indexes to provide higher optical transparency.

Furthermore preferably, the components (1) to (4) each have a refractive index of 1.450 to 1.480. If the components (1) to (4) each have a refractive index of 1.450 to 1.480, the components constituting the silicone composition have similar refractive indexes to provide higher optical transparency.

If the curable silicone composition according to the present invention is comprised of two types of constituent compositions, namely a base material containing the components (1) to (3) and a catalyst material containing the components (1), (3), and (4), it is also important to control the respective refractive indexes of the components contained in the base material and the catalyst material in order to express the optical transparency described above.

Preferably, among the components constituting the base material of the curable silicone composition according to the present invention, the components (1) and (3) each have a refractive index of 1.450 to 1.480. If the components (1) and (3) each have a refractive index of 1.450 to 1.480, the components constituting the base material of the curable silicone composition have similar refractive indexes to provide higher optical transparency.

More preferably, among the components constituting the base material, the components (1) to (3) each have a refractive index of 1.450 to 1.480. If the components (1) to (3) each have a refractive index of 1.450 to 1.480, the components constituting the base material of the curable silicone composition have similar refractive indexes to provide higher optical transparency.

Preferably, on the other hand, among the components constituting the catalyst material, the components (1) and (3) each have a refractive index of 1.450 to 1.480. If the components (1) and (3) each have a refractive index of 1.450 to 1.480, the components constituting the catalyst material of the curable silicone composition have similar refractive indexes to provide higher optical transparency.

Furthermore preferably, among the components constituting the catalyst material, the components (1), (3), and (4) each have a refractive index of 1.450 to 1.480. If the components (1), (3), and (4) each have a refractive index of 1.450 to 1.480, the components constituting the catalyst material of the curable silicone composition have similar refractive indexes to provide higher optical transparency.

Use of the curable silicone composition according to the present invention makes it possible not only to easily restore a complicated morphology, but also to shorten the time to be spent to fabricate it. The method of fabricating a molded material in various fields using the curable silicone composition according to the present invention will be described below. The method of fabricating a molded material using the curable silicone composition according to the present invention is a method of fabricating a molded material having a target form of an object, and includes a step of preparing the curable silicone composition according to the present invention by hand mixing, a step of pressing the prepared curable silicone composition onto an object with a form to be duplicated, a step of fabricating a concave mold to which the form of the object has been duplicated by curing the curable silicone composition pressed onto the object, a step of filling the concave mold with a photocurable resin, and a step of curing the photocurable resin injected into the concave mold by illuminating photocurable resin with light.

The term "target form" (form desired to be fabricated) of the object refers to forms of artificial nails, forms of a part or all of accessories, forms of ornaments such as buttons and brooches to be attached to clothing, forms of decorations and small articles to be used for gardening, forms of outer frames of key rings and key rings themselves, forms of models such as figures, and forms of toys and dental prosthetic restorations. The method according to the present invention is particularly useful for complicated forms that require time and skill for fabrication.

The term "duplicate" as used in the context of the present invention refers to obtaining a concave mold of a form to be fabricated by pressing the curable silicone composition according to the present invention which has been mixed onto a target form of an object.

The term "photocurable resin" as used in the context of the present invention refers to a material containing a resin to be polymerized and cured by illumination with light at a wavelength in the ultraviolet-visible range. Examples of the photocurable resin include a photocurable resin for nails, a photocurable resin for fabricating accessories, a photocurable resin for clothing ornaments, a photocurable resin for gardening, a photocurable resin for fabricating key rings, a photocurable resin for fabricating models, a photocurable resin for fabricating toys, and a photocurable resin for dental use.

If the molded material is a dental prosthetic restoration, the "target form of an object" refers to a tooth crown morphology in the oral cavity of a patient, an occlusal morphology, a cervical morphology, a frame morphology, a gingiva morphology, a mucous membrane morphology, a margin morphology, and a contour morphology. The fabrication method in which a dental prosthetic restoration is molded using the curable silicone composition according to the present invention is particularly useful to fabricate portions that require time and skill for restoration such as a tooth crown morphology and an occlusal morphology.

Examples of the photocurable resin used to fabricate a dental prosthetic restoration include a dental metal adhesive, a tooth surface coating material, a dental adhesive resin cement, a dental composite resin adhesive, a dental dentin adhesive, a dental hybrid resin, a dental ceramics adhesive, a dental composite resin, a polymer-based bracket adhesive, a tooth surface conditioning material, a dental core build-up material, a polymer-based dental pit-and-fissure sealant material, a dental opaque material, a polymer-based coloring material, a dental glazing and coating material, a dental resin-based modeling material, and other dental restorative materials. The method according to the present invention is particularly useful to prepare a complex morphology using a dental hybrid resin, a dental composite resin, a polymer-based dental pit-and-fissure sealant material, a dental resin-based modeling material, and so forth.

The method of fabricating a molded material using the curable silicone composition according to the present invention makes it possible, for even unskilled workers, not only to easily fabricate a complicated form, but also to shorten the time to be spent to fabricate it. If the method were not used, it would be significantly difficult for unskilled workers to fabricate a complicated form, and the workers may take a long time for the work, or may not be able to fabricate a molded material with a form desired to be fabricated. It may take a long time for even skilled workers to fabricate a complicated form.

When a dental prosthetic restoration is to be fabricated by a method of fabricating a molded material using the curable silicone composition according to the present invention, the conventional build-up method may be used concurrently. The method may be not only practiced on a tooth row model of a patient at a dental laboratory, but also practiced in the oral cavity of a patient at a dental clinic. Examples of fabrication of a dental prosthetic restoration will be described below. However, the present invention is not limited thereto.

Fabrication Example 1 of Dental Prosthetic Restoration

In order to perform a dental treatment using a dental prosthetic restoration, a dentist removes a portion to be treated in the oral cavity of a patient, and prepares an abutment tooth or prepares a cavity.

Then, a dental impression material is pressed onto a target portion in the oral cavity of the patient and a rubber elastic body is formed after a certain time elapses. By thereafter removing the elastic body from inside the oral cavity, an impression to which the shape of the oral cavity and teeth of the patient has been duplicated is obtained.

Gypsum slurry is poured into the obtained impression to obtain a gypsum model which has the morphology of the abutment tooth or the cavity formed in the oral cavity of the patient.

The obtained gypsum model is delivered to a dental technician, and the dental technician fabricates a dental prosthetic restoration based on the gypsum model. The dentist may deliver the impression to the dental technician, and the dental technician may fabricate the gypsum model.

The dental technician applies a thermoplastic resin or the like to the abutment tooth portion or the cavity portion of the gypsum model received from the dentist to restore a morphology desired to be finally fabricated. The curable silicone composition according to the present invention which has been mixed is pressed onto the thermoplastic resin, and left to stand for a certain time until the curable silicone composition is cured.

After the curable silicone composition is cured, the thermoplastic resin at the abutment tooth portion or the cavity portion of the gypsum model is removed, and a photocurable resin is injected into the concave mold of the curable silicone composition. The photocurable resin is pressed onto the abutment tooth portion or the cavity portion of the gypsum model, and illuminated with light using a light curing machine to incompletely polymerize the photocurable resin.

After the incomplete polymerization is performed to the extent that the photocurable resin can be removed from the curable silicone composition without deformation of the molded material obtained by curing the photocurable resin, the molded material formed of the photocurable resin is removed from the curable silicone composition, and then is completely polymerized using the light curing machine again. After the molded material formed of the photocurable resin is sufficiently cured, the surface of the molded material formed of the photocurable resin is characterized, finally adjusted, and finally polished.

Fabrication Example 2 of Dental Prosthetic Restoration

If a tooth crown morphology desired to be fabricated is maintained in the oral cavity of a patient, a dentist fabricates in advance a concave mold with the morphology desired to be fabricated using the curable silicone composition according to the present invention before treatment (preparation of an abutment tooth or preparation of a cavity).

The photocurable resin is injected into the obtained concave mold of the curable silicone composition according to the present invention, pressed onto a portion in the oral cavity of the patient that has been subjected to the treatment (preparation of an abutment tooth or preparation of a cavity), and illuminated with light using a light curing machine to incompletely polymerize the photocurable resin.

After the incomplete polymerization is performed to the extent that the photocurable resin can be removed from the curable silicone composition without deformation of the molded material obtained by curing the photocurable resin, the molded material formed of the photocurable resin is removed from inside the oral cavity of the patient, and the photocurable resin is completely polymerized using the light curing machine again. After the molded material formed of the photocurable resin is sufficiently cured, the surface of the molded material is characterized, finally adjusted, and finally polished.

EXAMPLES

Examples and comparative examples of the present invention will be described below. The present invention is not limited to the examples described below.

The method of evaluating the curable silicone compositions according to the examples and the comparative examples will be described in detail below.

[Measurement of Complex Viscosity]

The complex viscosity of the base material and the catalyst material of the curable silicone compositions according to the examples and the comparative examples described below was measured using a rheometer Physica MCR 301 manufactured by Anton Paar at a stage temperature of 23° C., a strain amount of 1%, and a frequency of 0.1 Hz to 100 Hz, by frequency dispersion measurement at an angular frequency of 25 rad/s.

[Evaluation of Form]

If the curable silicone composition was hand-mixable, the curable silicone composition was evaluated to be in a putty form. If the viscosity of the curable silicone composition was so low that the curable silicone composition was not easily hand-mixable, the curable silicone composition was evaluated to be in a pasty form.

[Mixing Ratio (Catalyst Material:Base Material)]

The mixing ratio by weight between the catalyst material and the base material is indicated.

[Measurement of Optical Transmittance]

A mixture obtained by hand-mixing the base material and the catalyst material of the curable silicone compositions according to the examples and the comparative examples described below was poured into a mold with an inside diameter of 30 mm and a thickness of 2 mm placed on a glass plate. Immediately after that, a glass plate, which was identical to the glass plate on which the mold was placed, was put on the mold and pressed at 10 kg/cm². The mold was left to stand under the same pressure conditions until the mixture was cured to fabricate a silicone composition specimen for optical transmittance measurement. The fabricated specimen was measured for transmittance at a wavelength of 470 nm at 23° C. using a spectrophotometer CM-3500d manufactured by Konica Minolta, Inc.

[Measurement of Depth of Cure]

A mixture obtained by hand-mixing the base material and the catalyst material of the curable silicone compositions according to the examples and the comparative examples described below was poured into a mold with an inside diameter of 12 mm and a thickness of 16 mm placed on a glass plate. Immediately after that, a glass plate that was identical to the glass plate on which the mold was placed was put on the mold and was pressed at 5 kg/cm². The mold was left to stand under the same pressure conditions until the mixture was cured to fabricate a cured body of a silicone composition. Next, a photocurable resin (Solidex Incisal 59 manufactured by Shofu Inc.) was poured into a mold with an inside diameter of 4 mm and a thickness of 6 mm placed on a glass plate. Immediately after that, a glass plate that was identical to the glass plate on which the mold was placed was put on the mold and was pressed. The cured body of the curable silicone composition obtained earlier was pressed from above the glass plate on the mold. The photocurable resin was illuminated with light for 30 seconds using a light curing machine (Solidelite V manufactured by Shofu Inc.) to be cured. The photocurable resin was taken out of the mold, and an unpolymerized portion was removed to measure the thickness of a cured portion.

[Measurement of Flowability]

The flowability was measured according to a consistency test of JIS T 6513:2005, Dental elastomeric impression materials.

[Evaluation of Mixability]

The mixability for hand mixing of the base material and the catalyst material of the curable silicone compositions according to the examples and the comparative examples described below was evaluated. If the curable silicone composition was easily mixed with a small force until the base material and the catalyst material were uniformly mixed without a large resistance, the mixability of the curable silicone composition was evaluated to be "good". If the curable silicone composition was easily mixed until the base material and the catalyst material were uniformly mixed though with a slight resistance, the mixability of the curable silicone composition was evaluated to be "slightly heavy". If the curable silicone composition was mixed with a practically tolerable force until the base material and the catalyst material were uniformly mixed though with a large resistance, the mixability of the curable silicone composition was evaluated to be "heavy". If the curable silicone composition required a significantly strong, practically intolerable force until the base material and the catalyst material were uniformly mixed with a significantly large resistance, the mixability of the curable silicone composition was evaluated to be "very heavy".

[Evaluation of Stickiness]

The base material and the catalyst material of the curable silicone compositions according to the examples and the comparative examples described below were hand-mixed. If the paste did not remain on the fingers and no stickiness was felt when the paste was removed from the fingers, the curable silicone composition was evaluated as "non-sticky". If the paste remained on the fingers and stickiness was felt when the paste was removed from the fingers, the curable silicone composition was evaluated as "sticky".

[Working Time]

The base material and the catalyst material of the curable silicone compositions according to the examples and the comparative examples described below were mixed until the materials were uniformly mixed. The surface of the mixture was pulled using a metal spatula every 10 seconds to tactually perceive expression of rubber elasticity. The time taken from the start of mixing to the expression of rubber elasticity minus 10 seconds was determined as the working time.

[Comprehensive Evaluation]

In comprehensive consideration of the evaluation items discussed above, curable silicone compositions particularly suitable for use for the present invention were evaluated as "○", curable silicone compositions usable for the present invention were evaluated as "Δ", and curable silicone compositions not usable for the present invention were evaluated as "x".

[Details of Components Used to Prepare Curable Silicone Composition]

The refractive indexes of the components (1) to (4) used to prepare the curable silicone composition according to the present invention are shown in Table 1. For the component (3) as a filler, the 50% particle size and the shape are also shown. The characteristics were measured as follows.

TABLE 1

|  |  | Refractive index | 50% particle size/μm | Shape |
|---|---|---|---|---|
| Component (1) | α,ω-divinylpolydimethyldiphenylsiloxane | 1.463 | — | — |
|  | α,ω-divinylpolydimethylsiloxane | 1.405 | — | — |
|  | α,ω-divinylpolydimethyldiethylsiloxane | 1.413 | — | — |
| Component (2) | Dimethyldiphenylhydrogenpolysiloxane | 1.464 | — | — |
|  | Dimethylhydrogenpolysiloxane | 1.401 | — | — |
|  | Methyloctanylhydrogenpolysiloxane | 1.442 | — | — |
| Component (3) | Amorphous silica 1 | 1.460 | 1 | Spherical |
|  | Amorphous silica 2 | 1.460 | 15 | Spherical |
|  | Amorphous silica 3 | 1.460 | 7 | Spherical |
|  | Amorphous silica 4 | 1.460 | 0.09 | Spherical |
|  | Amorphous silica 5 | 1.460 | 2 | Indefinite |
|  | Crystalline silica | 1.540 | 7 | Indefinite |
|  | Calcium fluoride | 1.430 | 30 | Indefinite |
| Component (4) | Platinum catalyst 1 | 1.411 | — | — |
|  | Platinum catalyst 2 | 1.465 | — | — |
|  | Platinum catalyst 3 | 1.543 | — | — |

Refractive index: The refractive index was measured at a stage temperature of 26 to 28° C. using an Abbe refractometer manufactured by Atago Co., Ltd.

50% Particle size: The 50% particle size was measured using a particle size analyzer Microtrac ERA manufactured by Honeywell.

Shape: The shape was measured by capturing a photograph of particles using a scanning or transmission electron microscope to measure the uniformity ratio of the particles.

[Preparation of Curable Silicone Composition]

The compounding ratio of the constituent compositions (the base material and the catalyst material) of the curable silicone compositions and the complex viscosity of the constituent compositions are shown in Tables 2 to 10. For Comparative Example 1, as shown in Table 11, the difference among the refractive indexes of the components (1) to (3) is more than 0.100. For Comparative Examples 2 to 4, the complex viscosity of the base material and the catalyst material as the constituent compositions is outside the range of 10 Pa·s to 100000 Pa·s. More particularly, the complex viscosity of both the base material and the catalyst material is less than the above range for Comparative Example 2, the complex viscosity of both the base material and the catalyst material is more than the above range for Comparative Example 3, and the complex viscosity of the base material is more than the above range and the complex viscosity of the catalyst material is less than the above range for Comparative Example 4.

TABLE 2

|  |  | Ex. 1 | | Comp. Ex. 1 | | Comp. Ex. 2 | | Comp. Ex. 3 | |
|---|---|---|---|---|---|---|---|---|---|
|  |  | Catalyst material | Base material | Catalyst material | Base material | Catalyst material | Base material | Catalyst material | Base material |
| Component (1) | α,ω-divinylpolydimethyl-diphenylsiloxane | 14.9 | 14.6 | 14.9 | 14.6 | 89.9 | 89.6 | 1.9 | 1.6 |
| Component (2) | Dimethylhydrogen-polysiloxane | — | 0.4 | — | 0.4 | — | 0.4 | — | 0.4 |
| Component (3) | Amorphous silica 1 | 85 | 85 | — | — | 10 | 10 | 98 | 98 |
|  | Crystalline silica | — | — | 85 | 85 | — | — | — | — |
| Component (4) | Platinum catalyst 1 | 0.1 | — | 0.1 | — | 0.1 | — | 0.1 | — |
|  | Total | 100 | 100 | 100 | 100 | 100 | 100 | 100 | 100 |
|  | Complex viscosity/Pa·s | 5580 | 2080 | 7650 | 5840 | 8 | 5 | 123000 | 111000 |

TABLE 3

|  |  | Ex. 2 | | Ex. 3 | | Ex. 4 | | Ex. 5 | |
|---|---|---|---|---|---|---|---|---|---|
|  |  | Catalyst material | Base material | Catalyst material | Base material | Catalyst material | Base material | Catalyst material | Base material |
| Component (1) | α,ω-divinylpolydimethyl-diphenylsiloxane | 69.9 | 69.6 | 54.9 | 54.6 | 69.9 | 69.6 | 14.9 | 14.6 |
| Component (2) | Dimethylhydrogen-polysiloxane | — | 0.4 | — | 0.4 | — | 0.4 | — | 0.4 |
| Component (3) | Amorphous silica 2 | 30 | 30 | — | — | — | — | — | — |
|  | Amorphous silica 3 | — | — | 45 | 45 | — | — | — | — |
|  | Amorphous silica 4 | — | — | — | — | 30 | 30 | — | — |
|  | Amorphous silica 5 | — | — | — | — | — | — | 85 | 85 |

TABLE 3-continued

|  |  | Ex. 2 | | Ex. 3 | | Ex. 4 | | Ex. 5 | |
| --- | --- | --- | --- | --- | --- | --- | --- | --- | --- |
|  |  | Catalyst material | Base material | Catalyst material | Base material | Catalyst material | Base material | Catalyst material | Base material |
| Component (4) | Platinum catalyst 1 | 0.1 | — | 0.1 | — | 0.1 | — | 0.1 | — |
|  | Total | 100 | 100 | 100 | 100 | 100 | 100 | 100 | 100 |
|  | Complex viscosity/Pa · s | 3990 | 2450 | 68 | 68 | 11900 | 9150 | 11600 | 8970 |

TABLE 4

|  |  | Ex. 6 | | Ex. 7 | | Ex. 8 | | Ex. 9 | |
| --- | --- | --- | --- | --- | --- | --- | --- | --- | --- |
|  |  | Catalyst material | Base material | Catalyst material | Base material | Catalyst material | Base material | Catalyst material | Base material |
| Component (1) | α,ω-divinylpolydimethyl-diphenylsiloxane | 3.9 | 3.6 | 49.9 | 49.6 | 84.9 | 84.6 | 89.9 | 89.6 |
| Component (2) | Dimethylhydrogen-polysiloxane | — | 0.4 | — | 0.4 | — | 0.4 | — | 0.4 |
| Component (3) | Amorphous silica 1 | 96 | 96 | — | — | — | — | — | — |
|  | Amorphous silica 2 | — | — | 50 | 50 | 15 | 15 | 10 | 10 |
| Component (4) | Platinum catalyst 1 | 0.1 | — | 0.1 | — | 0.1 | — | 0.1 | — |
|  | Total | 100 | 100 | 100 | 100 | 100 | 100 | 100 | 100 |
|  | Complex viscosity/Pa · s | 39900 | 31200 | 52900 | 50300 | 780 | 550 | 38 | 25 |

TABLE 5

|  |  | Ex. 10 | | Ex. 11 | | Ex. 12 | |
| --- | --- | --- | --- | --- | --- | --- | --- |
|  |  | Catalyst material | Base material | Catalyst material | Base material | Catalyst material | Base material |
| Component (1) | α,ω-divinylpolydimethyl-diphenylsiloxane | 69.9 | 69.6 | 69.9 | 69.6 | — | — |
|  | α,ω-divinylpolydimethyl-siloxane | — | — | — | — | 69.9 | 69.6 |
|  | Dimethylhydrogen-polysiloxane | — | — | — | — | — | 0.4 |
| Component (2) | Dimethyldiphenyl-hydrogenpolysiloxane | — | 0.4 | — | 0.4 | — | — |
| Component (3) | Amorphous silica 2 | 30 | 30 | 30 | 30 | 30 | 30 |
| Component (4) | Platinum catalyst 1 | 0.1 | — | — | — | 0.1 | — |
|  | Platinum catalyst 2 | — | — | 0.1 | — | — | — |
|  | Total | 100 | 100 | 100 | 100 | 100 | 100 |
|  | Complex viscosity/Pa · s | 3990 | 2450 | 3990 | 2450 | 3990 | 2450 |

TABLE 6

|  |  | Ex. 13 | | Ex. 14 | | Ex. 15 | |
| --- | --- | --- | --- | --- | --- | --- | --- |
|  |  | Catalyst material | Base material | Catalyst material | Base material | Catalyst material | Base material |
| Component (1) | α,ω-divinylpolydimethyl-diphenylsiloxane | — | — | 69.9 | 69.6 | 69.9 | 69.6 |
|  | α,ω-divinylpolydimethyl-diethylsiloxane | 69.9 | 69.6 | — | — | — | — |
|  | Dimethylhydrogen-polysiloxane | — | 0.4 | — | — | — | 0.4 |
| Component (2) | Methyloctanylhydrogen-polysiloxane | — | — | — | 0.4 | — | — |
| Component (3) | Amorphous silica 2 | 30 | 30 | 30 | 30 | — | — |
|  | Calcium fluoride | — | — | — | — | 30 | 30 |
| Component (4) | Platinum catalyst 1 | 0.1 | — | 0.1 | — | 0.1 | — |
|  | Total | 100 | 100 | 100 | 100 | 100 | 100 |
|  | Complex viscosity/Pa · s | 3990 | 2450 | 3990 | 2450 | 66 | 66 |

TABLE 7

|  |  | Ex. 16 | | Ex. 17 | |
|---|---|---|---|---|---|
|  |  | Catalyst material | Base material | Catalyst material | Base material |
| Component (1) | α,ω-divinylpoly-dimethyl diphenylsiloxane | 69.9 | 69.98 | 69.9 | 10 |
| Component (2) | Dimethyldiphenyl-hydrogen-polysiloxane | — | 0.02 | — | 60 |
| Component (3) | Amorphous silica 2 | 30 | 30 | 30 | 30 |
| Component (4) | Platinum catalyst 1 | 0.1 | — | 0.1 | — |
| Total | | 100 | 100 | 100 | 100 |
| Complex viscosity/Pa·s | | 4010 | 2460 | 3780 | 2330 |

TABLE 8

|  |  | Ex. 18 | | Ex. 19 | |
|---|---|---|---|---|---|
|  |  | Catalyst material | Base material | Catalyst material | Base material |
| Component (1) | α,ω-divinylpoly dimethyldiphenyl-siloxane | 69.99 | 69.6 | 69 | 69.6 |
| Component (2) | Dimethylhydrogen-polysiloxane | — | 0.4 | — | 0.4 |
| Component (3) | Amorphous silica 2 | 30 | 30 | 30 | 30 |
| Component (4) | Platinum catalyst 1 | 0.01 | — | 1 | — |
| Total | | 100 | 100 | 100 | 100 |
| Complex viscosity/Pa·s | | 3990 | 2450 | 3990 | 2450 |

TABLE 9

|  |  | Ex. 20 | |
|---|---|---|---|
|  |  | Catalyst material | Base material |
| Component (1) | α,ω-divinylpolydimethyl-diphenylsiloxane | 14.9 | 14.6 |
| Component (2) | Dimethylhydrogen-polysiloxane | — | 0.4 |
| Component (3) | Amorphous silica 1 | 85 | 85 |
| Component (4) | Platinum catalyst 3 | 0.1 | — |
| Total | | 100 | 100 |
| Complex viscosity/Pa·s | | 5580 | 2080 |

TABLE 10

|  |  | Ex. 21 | | Comp. Ex. 4 | |
|---|---|---|---|---|---|
|  |  | Catalyst material | Base material | Catalyst material | Base material |
| Component (1) | α,ω-divinylpoly-dimethyldiphenyl-siloxane | 99 | 7.8 | 99 | 1.6 |
| Component (2) | Dimethyl-hydrogen polysiloxane | — | 0.4 | — | 0.4 |
| Component (3) | Amorphous silica 1 | — | 91.8 | — | 98 |
| Component (4) | Platinum catalyst 1 | 1 | — | 1 | — |
| Total | | 100 | 100 | 100 | 100 |
| Complex viscosity/Pa·s | | 1 | 10690 | 1 | 111000 |

TABLE 11

|  |  | Complex viscosity [Pa·s] | Suitability of complex viscosity range | Refractive index difference | Suitability of refractive index difference |
|---|---|---|---|---|---|
| Ex. 1 | Catalyst material | 5580 | ○ | 0.062 | ○ |
|  | Base material | 2080 | | | |
| Ex. 2 | Catalyst material | 3990 | ○ | 0.062 | ○ |
|  | Base material | 2450 | | | |
| Ex. 3 | Catalyst material | 68 | ○ | 0.062 | ○ |
|  | Base material | 68 | | | |
| Ex. 4 | Catalyst material | 11900 | ○ | 0.062 | ○ |
|  | Base material | 9150 | | | |
| Ex. 5 | Catalyst material | 11600 | ○ | 0.062 | ○ |
|  | Base material | 8970 | | | |
| Ex. 6 | Catalyst material | 39900 | ○ | 0.062 | ○ |
|  | Base material | 31200 | | | |
| Ex. 7 | Catalyst material | 52900 | ○ | 0.062 | ○ |
|  | Base material | 50300 | | | |
| Ex. 8 | Catalyst material | 780 | ○ | 0.062 | ○ |
|  | Base material | 550 | | | |
| Ex. 9 | Catalyst material | 38 | ○ | 0.062 | ○ |
|  | Base material | 25 | | | |
| Ex. 10 | Catalyst material | 3990 | ○ | 0.004 | ○ |
|  | Base material | 2450 | | | |
| Ex. 11 | Catalyst material | 3990 | ○ | 0.004 | ○ |
|  | Base material | 2450 | | | |
| Ex. 12 | Catalyst material | 3990 | ○ | 0.059 | ○ |
|  | Base material | 2450 | | | |
| Ex. 13 | Catalyst material | 3990 | ○ | 0.059 | ○ |
|  | Base material | 2450 | | | |
| Ex. 14 | Catalyst material | 3990 | ○ | 0.021 | ○ |
|  | Base material | 2450 | | | |
| Ex. 15 | Catalyst material | 66 | ○ | 0.062 | ○ |
|  | Base material | 66 | | | |
| Ex. 16 | Catalyst material | 4010 | ○ | 0.004 | ○ |
|  | Base material | 2460 | | | |
| Ex. 17 | Catalyst material | 3780 | ○ | 0.004 | ○ |
|  | Base material | 2330 | | | |
| Ex. 18 | Catalyst material | 3990 | ○ | 0.062 | ○ |
|  | Base material | 2450 | | | |
| Ex. 19 | Catalyst material | 3990 | ○ | 0.062 | ○ |
|  | Base material | 2450 | | | |
| Ex. 20 | Catalyst material | 5580 | ○ | 0.062 | ○ |
|  | Base material | 2080 | | | |
| Ex. 21 | Catalyst material | 1 | ○ | 0.062 | ○ |
|  | Base material | 10690 | | | |
| Comp. Ex. 1 | Catalyst material | 7650 | ○ | 0.139 | x |
|  | Base material | 5840 | | | |
| Comp. Ex. 2 | Catalyst material | 8 | x | 0.062 | ○ |
|  | Base material | 5 | | | |
| Comp. Ex. 3 | Catalyst material | 123000 | x | 0.062 | ○ |
|  | Base material | 111000 | | | |
| Comp. Ex. 4 | Catalyst material | 1 | x | 0.062 | ○ |
|  | Base material | 111000 | | | |

Examples 1 to 21 and Comparative Examples 1 to 4

The prepared constituent compositions (the base material and the catalyst material) of the curable silicone compositions were mixed at a predetermined mixing ratio, and thereafter the curable silicone compositions were subjected to the various characteristic tests discussed earlier. The test results are shown in Tables 12 to 20.

The conditions for Example 1 and Comparative Examples 1 to 3 are shown in Table 2, and the test results for such examples are shown in Table 12.

TABLE 12

|  | Ex. 1 | | Com. Ex. 1 | | Com. Ex. 2 | | Com. Ex. 3 | |
| --- | --- | --- | --- | --- | --- | --- | --- | --- |
|  | Catalyst material | Base material | Catalyst material | Base material | Catalyst material | Base material | Catalyst material | Base material |
| Form | Putty | Putty | Putty | Putty | Pasty | Pasty | Putty | Putty |
| Mixing ratio (catalyst:base) | 1:1 | | 1:1 | | 1:1 | | 1:1 | |
| Optical transmittance (470 nm)/% | 65 | | 20 | | 93 | | 30 | |
| Depth of cure/mm | 1.2 | | Unmeasurable | | 1.9 | | Unmeasurable | |
| Flowability/mm | 25 | | 18 | | 50 | | 10 | |
| Mixability | Good | | Slightly heavy | | Unmixable | | Very heavy | |
| Stickiness | Non-sticky | | Non-sticky | | — | | Non-sticky | |
| Working time/s | 60 | | 60 | | 80 | | 60 | |
| Comprehensive evaluation | ○ | | x | | x | | x | |

The composition according to Example 1 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 60 seconds, and a sufficient time to keep its workable flowability was secured.

The composition according to Comparative Example 1 was the same as the composition according to Example 1 except that the component (3) as a filler was changed to crystalline silica (refractive index: 1.54), the difference between the refractive index of which and the refractive index of dimethylhydrogenpolysiloxane (refractive index: 1.401) as the component (2) was 0.100 or more. The composition according to Comparative Example 1 had a low transmittance of 20% at a wavelength of 470 nm and the photocurable resin was not cured to a sufficient depth of cure. As a result, it was not possible to fabricate a specimen. In addition, although a non-sticky composition in a putty form was obtained, the composition had slightly heavy mixability, and the mixture had slightly low flowability. The working time was 60 seconds, and a sufficient time to keep its workable flowability was secured.

The composition according to Comparative Example 2 contained a smaller amount of amorphous silica 1, and the complex viscosity of the base material and the catalyst material was less than 10 Pa·s. The composition according to Comparative Example 2 had a high transmittance of 50% or more at a wavelength of 470 nm and a depth of cure of 1 mm or more, and had an optical transmittance enough to incompletely polymerize the photocurable resin. However, the composition had a low complex viscosity and was not obtained in a putty form, and therefore was not hand-mixable. In addition, the mixture had so high flowability that the mixture flows because of its own weight, and therefore desirable formativity was not obtained. The working time was 80 seconds, and a sufficient time to keep its workable flowability was secured.

The composition according to Comparative Example 3 contained a larger amount of amorphous silica 1, and the complex viscosity of the base material and the catalyst material was more than 100000 Pa·s. The composition according to Comparative Example 3 had a low transmittance of 30% at a wavelength of 470 nm and the photocurable resin was not cured to a sufficient depth of cure. As a result, it was not possible to fabricate a specimen. In addition, although a non-sticky composition in a putty form was obtained, the composition had significantly heavy mixability, the mixture had significantly low flowability, and therefore desirable characteristics were not obtained. The working time was 60 seconds, and a sufficient time to keep its workable flowability was secured.

The conditions for Examples 2 to 5 are shown in Table 3, and the test results for such examples are shown in Table 13.

TABLE 13

|  | Ex. 2 | | Ex. 3 | | Ex. 4 | | Ex. 5 | |
| --- | --- | --- | --- | --- | --- | --- | --- | --- |
|  | Catalyst material | Base material | Catalyst material | Base material | Catalyst material | Base material | Catalyst material | Base material |
| Form | Putty | Putty | Putty | Putty | Putty | Putty | Putty | Putty |
| Mixing ratio (catalyst:base) | 1:1 | | 1:1 | | 1:1 | | 1:1 | |
| Optical transmittance (470 nm)/% | 86 | | 85 | | 85 | | 61 | |
| Depth of cure/mm | 1.7 | | 1.7 | | 1.6 | | 1.1 | |
| Flowability/mm | 31 | | 35 | | 17 | | 15 | |

TABLE 13-continued

|  | Ex. 2 | | Ex. 3 | | Ex. 4 | | Ex. 5 | |
| --- | --- | --- | --- | --- | --- | --- | --- | --- |
|  | Catalyst material | Base material | Catalyst material | Base material | Catalyst material | Base material | Catalyst material | Base material |
| Mixability | Good | | Good | | Good | | Heavy | |
| Stickiness | Non-sticky | | Non-sticky | | Sticky | | Non-sticky | |
| Working time/s | 60 | | 60 | | 60 | | 60 | |
| Comprehensive evaluation | ○ | | ○ | | Δ | | Δ | |

In Examples 2 to 5, amorphous silica 2 with a larger 50% particle size (50% particle size: 15 μm), amorphous silica 3 (50% particle size: 7 μm), amorphous silica 4 with a smaller 50% particle size (50% particle size: 0.09 μm), and amorphous silica 5 in an indefinite shape (50% particle size: 2 μm), respectively, were used as the component (3) as a filler in place of the amorphous silica 1 used in Example 1. In Examples 2 to 5, amorphous silica with different 50% particle sizes was used, and therefore the content of the amorphous silica in the total composition may be different from that in Example 1.

The composition according to Example 2 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 60 seconds, and a sufficient time to keep its workable flowability was secured.

The composition according to Example 3 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 60 seconds, and a sufficient time to keep its workable flowability was secured.

The composition according to Example 4 had a high transmittance of 50% or more at a wavelength of 470 nm and a depth of cure of 1 mm or more, and had an optical transmittance enough to incompletely polymerize the photocurable resin. In addition, although a composition in a putty form with good mixability was obtained, the mixture had slightly low flowability, and was sticky. The working time was 60 seconds, and a sufficient time to keep its workable flowability was secured.

The composition according to Example 5 had a high transmittance of 50% or more at a wavelength of 470 nm and a depth of cure of 1 mm or more, and had an optical transmittance enough to incompletely polymerize the photocurable resin. In addition, although a non-sticky composition in a putty form was obtained, the composition had heavy mixability, and the mixture had low flowability. The working time was 60 seconds, and a sufficient time to keep its workable flowability was secured.

The conditions for Examples 6 to 9 are shown in Table 4, and the test results for such examples are shown in Table 14.

TABLE 14

|  | Ex. 6 | | Ex. 7 | | Ex. 8 | | Ex. 9 | |
| --- | --- | --- | --- | --- | --- | --- | --- | --- |
|  | Catalyst material | Base material | Catalyst material | Base material | Catalyst material | Base material | Catalyst material | Base material |
| Form | Putty | Putty | Putty | Putty | Putty | Putty | Putty | Putty |
| Mixing ratio (catalyst:base) | 1:1 | | 1:1 | | 1:1 | | 1:1 | |
| Optical transmittance (470 nm)/% | 52 | | 62 | | 94 | | 95 | |
| Depth of cure/mm | 1 | | 1.2 | | 2.1 | | 2.1 | |
| Flowability/mm | 17 | | 14 | | 34 | | 36 | |
| Mixability | Slightly heavy | | Heavy | | Good | | Good | |
| Stickiness | Non-sticky | | Non-sticky | | Sticky | | Sticky | |
| Working time/s | 60 | | 60 | | 60 | | 70 | |
| Comprehensive evaluation | Δ | | Δ | | Δ | | Δ | |

The composition according to Example 6 was obtained by changing the content of the amorphous silica 1 from that for the composition according to Example 1 such that the content of the amorphous silica 1 in the total composition was more than 95 wt %. The composition according to Example 6 had a high transmittance of 50% or more at a wavelength of 470 nm and a depth of cure of mm or more, and had an optical transmittance enough to incompletely polymerize the photocurable resin. In addition, although a non-sticky composition in a putty form was obtained, the composition had slightly heavy mixability, and the mixture had slightly low flowability. The working time was 60 seconds, and a sufficient time to keep its workable flowability was secured.

The composition according to Example 7 was obtained by changing the content of the amorphous silica 2 from that for the composition according to Example 2 such that the complex viscosity of the base material and the catalyst material is 50000 Pa·s to 100000 Pa·s. The composition according to Example 7 had a high transmittance of 50% or more at a wavelength of 470 nm and a depth of cure of 1 mm or more, and had an optical transmittance enough to incompletely polymerize the photocurable resin. In addition, although a non-sticky composition in a putty form was obtained, the composition had heavy mixability, and the mixture had low flowability. The working time was 60 seconds, and a sufficient time to keep its workable flowability was secured.

The composition according to Example 8 was obtained by changing the content of the amorphous silica 2 from that for the composition according to Example 2 such that the content of the amorphous silica 2 in the total composition was 15 wt %, the content of α,ω-divinyipolydimethyldiphenyisiloxane was 80 wt % or more, and the complex viscosity of the base material and the catalyst material was less than 1000 Pa·s. The composition according to Example 8 had a high transmittance of 50% or more at a wavelength of 470 nm and a depth of cure of 1 mm or more, and had an optical transmittance enough to incompletely polymerize the photocurable resin. In addition, although the composition was in a putty form and had good mixability, and the mixture had desirable flowability, the composition was sticky. The working time was seconds, and a sufficient time to keep its workable flowability was secured.

The composition according to Example 9 was obtained by changing the content of the amorphous silica 2 from that for the composition according to Example 2 such that the content of the amorphous silica 2 in the total composition was 10 wt %, the content of α,ω-divinylpolydimethyldiphenylsiloxane was more than 85 wt %, and the complex viscosity of the base material and the catalyst material was less than 50 Pa·s. The composition according to Example 9 had a high transmittance of 50% or more at a wavelength of 470 nm and a depth of cure of 1 mm or more, and had an optical transmittance enough to incompletely polymerize the photocurable resin. In addition, although the composition was in a putty form and had good mixability, and the mixture had desirable flowability, the composition was sticky. The working time was 70 seconds, and a sufficient time to keep its workable flowability was secured.

The conditions for Examples 10 to 12 are shown in Table 5, and the test results for such examples are shown in Table 15.

TABLE 15

| | Ex. 10 | | Ex. 11 | | Ex. 12 | |
| --- | --- | --- | --- | --- | --- | --- |
| | Catalyst material | Base material | Catalyst material | Base material | Catalyst material | Base material |
| Form | Putty | Putty | Putty | Putty | Putty | Putty |
| Mixing ratio (catalyst:base) | 1:1 | | 1:1 | | 1:1 | |
| Optical transmittance (470 nm)/% | 90 | | 92 | | 45 | |
| Depth of cure/mm | 1.9 | | 2 | | 0.9 | |
| Flowability/mm | 31 | | 31 | | 31 | |
| Mixability | Good | | Good | | Good | |
| Stickiness | Non-sticky | | Non-sticky | | Non-sticky | |
| Working time/s | 80 | | 80 | | 70 | |
| Comprehensive evaluation | ○ | | ○ | | Δ | |

The composition according to Example 10 was obtained by changing the type of the component (2) from that for the composition according to Example 2 such that the refractive indexes of the components (1) to (3) were in the range of 1.450 to 1.480. The composition according to Example 10 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 80 seconds, and a sufficient time to keep its workable flowability was secured.

The composition according to Example 11 was obtained by changing the type of the component (4) from that for the composition according to Example 10 such that the refractive indexes of the components (1) to (4) were in the range of 1.450 to 1.480. The composition according to Example 11 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 80 seconds, and a sufficient time to keep its workable flowability was secured.

The composition according to Example 12 was obtained by changing the type of the component (1) from that for the composition according to Example 2 such that the refractive indexes of the component (3) was in the range of 1.450 to 1.480 and the refractive indexes of the components (1), (2), and (4) were outside the range of 1.450 to 1.480. The composition according to Example 12 had a low transmittance of 45% at a wavelength of 470 nm, and has a depth of cure of less than 1 mm. The composition was in a putty form and non-sticky and had good mixability, and the mixture had desirable flowability. The working time was 70 seconds, and a sufficient time to keep its workable flowability was secured.

The conditions for Examples 13 to 15 are shown in Table 6, and the test results for such examples are shown in Table 16.

TABLE 16

| | Ex. 13 | | Ex. 14 | | Ex. 15 | |
| --- | --- | --- | --- | --- | --- | --- |
| | Catalyst material | Base material | Catalyst material | Base material | Catalyst material | Base material |
| Form | Putty | Putty | Putty | Putty | Putty | Putty |
| Mixing ratio (catalyst:base) | 1:1 | | 1:1 | | 1:1 | |
| Optical transmittance (470 nm)/% | 50 | | 88 | | 45 | |
| Depth of cure/mm | 1 | | 1.7 | | 0.9 | |
| Flowability/mm | 31 | | 31 | | 34 | |
| Mixability | Good | | Good | | Good | |
| Stickiness | Non-sticky | | Non-sticky | | Non-sticky | |
| Working time/s | 50 | | 200 | | 60 | |
| Comprehensive evaluation | ○ | | Δ | | Δ | |

The composition according to Example 13 was obtained by changing the type of the component (1) from that for the composition according to Example 2 to α,ω-divinylpolydimethyldiethylsiloxane not containing an aromatic hydrocarbon group in its side chain. The composition according to Example 13 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 50 seconds, and a sufficient time to keep its workable flowability was secured.

The composition according to Example 14 was obtained by changing the type of the component (2) from that for the composition according to Example 2 to methyloctanylhydrogenpolysiloxane not containing an aromatic hydrocarbon group in its side chain. The composition according to Example 14 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 200 seconds, and a sufficient time to keep its workable flowability was secured although the composition was cured slightly slowly.

The composition according to Example 15 was obtained by changing the type of the component (3) from that for the composition according to Example 2 to calcium fluoride which was not amorphous silica. The composition according to Example 15 had a low transmittance of 45% at a wavelength of 470 nm, and has a depth of cure of less than 1 mm. In addition, the composition was in a putty form and non-sticky and had good mixability, and the mixture had desirable flowability. The working time was 60 seconds, and a sufficient time to keep its workable flowability was secured.

The conditions for Examples 16 and 17 are shown in Table 7, and the test results for such examples are shown in Table 17.

TABLE 17

|  | Ex. 16 | | Ex. 17 | |
| --- | --- | --- | --- | --- |
|  | Catalyst material | Base material | Catalyst material | Base material |
| Form | Putty | Putty | Putty | Putty |
| Mixing ratio (catalyst:base) | 1:1 | | 1:1 | |
| Optical transmittance (470 nm)/% | 90 | | 88 | |
| Depth of cure/mm | 1.9 | | 1.8 | |
| Flowability/mm | 31 | | 32 | |
| Mixability | Good | | Good | |
| Stickiness | Non-sticky | | Non-sticky | |
| Working time/s | 600 or more | | Less than 20 | |
| Comprehensive evaluation | Δ | | Δ | |

For the composition according to Example 16, the content of the component (2) in the total composition was 0.01 wt %. The composition according to Example 16 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. However, the working time was 600 seconds or more, and it took slightly too long a time before rubber elasticity is expressed.

For the composition according to Example 17, the content of the component (2) in the total composition was 30 wt %. The composition according to Example 17 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. However, the working time was less than 20 seconds, and the time to keep its workable flowability was slightly too short.

The conditions for Examples 18 and 19 are shown in Table 8, and the test results for such examples are shown in Table 18.

TABLE 18

|  | Ex. 18 | | Ex. 19 | |
| --- | --- | --- | --- | --- |
|  | Catalyst material | Base material | Catalyst material | Base material |
| Form | Putty | Putty | Putty | Putty |
| Mixing ratio (catalyst:base) | 1:1 | | 1:1 | |
| Optical transmittance (470 nm)/% | 87 | | 84 | |
| Depth of cure/mm | 1.7 | | 1.6 | |
| Flowability/mm | 31 | | 31 | |
| Mixability | Good | | Good | |
| Stickiness | Non-sticky | | Non-sticky | |
| Working time/s | 600 or more | | Less than 20 | |
| Comprehensive evaluation | Δ | | Δ | |

For the composition according to Example 18, the content of the component (4) in the total composition was 0.005 wt %. The composition according to Example 18 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. However, the working time was 600 seconds or more, and it took slightly too long a time before rubber elasticity is expressed.

For the composition according to Example 19, the content of the component (4) in the total composition was 0.5 wt %. The composition according to Example 19 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. However, the working time was less than 20 seconds, and the time to keep its workable flowability was slightly too short.

The conditions for Example 20 are shown in Table 9, and the test results for such an example are shown in Table 19.

TABLE 19

|  | Ex. 20 | |
| --- | --- | --- |
|  | Catalyst material | Base material |
| Form | Putty | Putty |
| Mixing ratio (catalyst:base) | 1:1 | |
| Optical transmittance (470 nm)/% | 59 | |
| Depth of cure/mm | 1.1 | |
| Flowability/mm | 25 | |

TABLE 19-continued

| | Ex. 20 | |
| --- | --- | --- |
| | Catalyst material | Base material |
| Mixability | Good | |
| Stickiness | Non-sticky | |
| Working time/s | 60 | |
| Comprehensive evaluation | ○ | |

The composition according to Example 20 was obtained by using a platinum catalyst 3, the difference between the refractive index of which and the refractive index of dimethylhydrogenpolysiloxane (refractive index: 1.401) as the component (2) was 0.1000 or more, in place of the platinum catalyst 1 as the component (4) used in Example 1. The composition according to Example 20 had a high transmittance of 50% or more at a wavelength of 470 nm and a depth of cure of 1 mm or more, and had an optical transmittance enough to incompletely polymerize the photocurable resin. In addition, the composition was in a putty form and non-sticky and had good mixability, and the mixture had desirable flowability. The working time was 60 seconds, and a sufficient time to keep its workable flowability was secured.

The conditions for Example 21 and Comparative Example 4 are shown in Table 10, and the test results for such examples are shown in Table 20.

TABLE 20

| | Ex. 21 | | Comp. Ex. 4 | |
| --- | --- | --- | --- | --- |
| | Catalyst material | Base material | Catalyst material | Base material |
| Form | Pasty | Putty | Pasty | Putty |
| Mixing ratio (catalyst:base) | 1:10 | | 1:10 | |
| Optical transmittance (470 nm)/% | 57 | | 30 | |
| Depth of cure/mm | 1.1 | | Unmeasurable | |
| Flowability/mm | 18 | | 11 | |
| Mixability | Slightly heavy | | Very heavy | |
| Stickiness | Sticky | | Sticky | |
| Working time/s | 80 | | 80 | |
| Comprehensive evaluation | Δ | | x | |

For the composition according to Example 21, the complex viscosity of the catalyst material was 10 Pa·s or less and the complex viscosity of the base material was 10 Pa·s to 100000 Pa·s so that only one of the components constituting the curable silicone composition had a complex viscosity of 10 Pa·s to 100000 Pa·s. Because the complex viscosities of the catalyst material and the base material were greatly different from each other, the mixing ratio by weight between the catalyst material and the base material was set to 1:10. The composition according to Example 21 had a high transmittance of 50% or more at a wavelength of 470 nm and a depth of cure of 1 mm or more, and had an optical transmittance enough to incompletely polymerize the photocurable resin. In addition, although a composition in a putty form was obtained, stickiness was felt during mixing because the catalyst material was in a pasty form, the composition had slightly heavy mixability, and the mixture had slightly low flowability. The working time was 80 seconds, and a sufficient time to keep its workable flowability was secured.

For the composition according to Comparative Example 4, the complex viscosity of the catalyst material was 10 Pa·s or less and the complex viscosity of the base material was more than 100000 Pa·s so that all of the compositions constituting the curable silicone composition had a complex viscosity outside the range of 10 Pa·s to 100000 Pa·s. Because the complex viscosities of the catalyst material and the base material were greatly different from each other, the mixing ratio by weight between the catalyst material and the base material was set to 1:10. The composition according to Comparative Example 4 had a low transmittance of 30% at a wavelength of 470 nm and the photocurable resin was not cured to a sufficient depth of cure. As a result, it was not possible to fabricate a specimen. In addition, although a composition in a putty form was obtained, stickiness was felt during mixing because the catalyst material was in a pasty form, the composition had significantly heavy mixability, the mixture had significantly low flowability, and therefore desirable characteristics were not obtained. The working time was 80 seconds, and a sufficient time to keep its workable flowability was secured.

INDUSTRIAL APPLICABILITY

According to the present invention, it is possible to provide a curable silicone composition that has high optical transparency after being cured and that is in a putty form to be hand-mixable.

What is claimed is:

1. A curable silicone composition for dental prosthetics comprising:
    a base material containing a component (1), a component (2), and a component (3); and
    a catalyst material containing the component (1), the component (3), and a component (4),
wherein:
    the component (1) is an organopolysiloxane having at least two unsaturated groups in a molecule;
    the component (2) is an organohydrogenpolysiloxane having at least two SiH groups in a molecule;
    the component (3) is a filler
    the component (4) is a catalyst;
    components (1) and (3) each have a refractive index of 1.450 to 1.480;
    a difference between a refractive index of one of the components (1) to (3) that has the highest refractive index and a refractive index of one of the components (1) to (3) that has the lowest refractive index is 0.1000 or less; and
    a complex viscosity of each of the base material and the catalyst material of the curable silicon composition before the curable silicone composition is cured is 1000 Pa·s to 50000 Pa·s, as measured at a stage temperature of 23° C., a strain amount of 1%, and a frequency of 0.1 Hz to 100 Hz, by frequency dispersion measurement at an angular frequency of 25 rad/s.

2. The curable silicone composition according to claim 1, prepared by mixing the base material and the catalyst material.

3. The curable silicone composition according to claim 1, wherein in the total curable silicone composition,
    the component (1) accounts for 1 to 80 wt %;
    the component (2) accounts for 0.01 to 30 wt %;
    the component (3) accounts for 10 to 95 wt %; and
    the component (4) accounts for 0.005 to 0.5 wt %.

4. The curable silicone composition according to claim 1, wherein the components (2) and (4) each have a refractive index of 1.400 to 1.500.

5. The curable silicone composition according to claim 1, having an optical transmittance of 50% or more at a wavelength of 470 nm after being cured.

6. A method of fabricating a molded material comprising:
preparing the curable silicone composition according to claim 1;
fabricating a concave mold to which the form of an object has been duplicated by pressing the prepared curable silicone composition onto the object and curing the curable silicone composition; and
filling the concave mold with a photocurable resin, pressing the photocurable resin onto a portion to which the molded material is to be applied,
and illuminating the photocurable resin with light to cure the photocurable resin.

7. A base material of a curable silicone composition for dental prosthetics prepared by mixing the base material and a catalyst material, comprising:
organopolysiloxane having at least two unsaturated groups in a molecule as a component (1);
organohydrogenpolysiloxane having at least two SiH groups in a molecule as a component (2); and
a filler as a component (3), wherein:
components (1) and (3) each have a refractive index of 1.450 to 1.480;
a difference between a refractive index of one of the components (1) to (3) that has the highest refractive index and a refractive index of one of the components (1) to (3) that has the lowest refractive index is 0.1000 or less; and
a complex viscosity of the base material before the curable silicone composition is cured is 1000 Pa·s to 50000 Pa·s, as measured at a stage temperature of 23° C., a strain amount of 1%, and a frequency of 0.1 Hz to 100 Hz, by frequency dispersion measurement at an angular frequency of 25 rad/s.

8. A catalyst material of a curable silicone composition for dental prosthetics prepared by mixing a base material and the catalyst material, comprising:
organopolysiloxane having at least two unsaturated groups in a molecule as a component (1);
a filler as a component (3); and
a catalyst as a component (4), wherein:
components (1) and (3) each have a refractive index of 1.450 to 1.480; and
a complex viscosity of the catalyst material before the curable silicone composition is cured is 1000 Pa·s to 50000 Pa·s, as measured at a stage temperature of 23° C., a strain amount of 1%, and a frequency of 0.1 Hz to 100 Hz, by frequency dispersion measurement at an angular frequency of 25 rad/s.

9. The curable silicone composition according to claim 2, wherein in the total curable silicone composition,
the component (1) accounts for 1 to 80 wt %;
the component (2) accounts for 0.01 to 30 wt %;
the component (3) accounts for 10 to 95 wt %; and
the component (4) accounts for 0.005 to 0.5 wt %.

10. The curable silicone composition according to claim 2, wherein
the components (2) and (4) each have a refractive index of 1.400 to 1.500.

11. The curable silicone composition according to claim 3, wherein
the components (2) and (4) each have a refractive index of 1.400 to 1.500.

12. The curable silicone composition according to claim 2, having an optical transmittance of 50% or more at a wavelength of 470 nm after being cured.

13. The curable silicone composition according to claim 3, having an optical transmittance of 50% or more at a wavelength of 470 nm after being cured.

14. The curable silicone composition according to claim 4, having an optical transmittance of 50% or more at a wavelength of 470 nm after being cured.

\* \* \* \* \*